US008727575B2

(12) United States Patent
Nakabayashi et al.

(10) Patent No.: US 8,727,575 B2
(45) Date of Patent: May 20, 2014

(54) LIGHT SOURCE UNIT

(75) Inventors: Hitoshi Nakabayashi, Hyogo-ken (JP);
Akihisa Morimoto, Hyogo-ken (JP);
Takehiko Iguchi, Hyogo-ken (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 229 days.

(21) Appl. No.: 13/215,518

(22) Filed: Aug. 23, 2011

(65) Prior Publication Data
US 2012/0051059 A1    Mar. 1, 2012

(30) Foreign Application Priority Data

Aug. 30, 2010 (JP) ................................. 2010-191774
Sep. 22, 2010 (JP) ................................. 2010-211664

(51) Int. Cl.
*F21V 7/00* (2006.01)
*F21V 5/00* (2006.01)
*F21V 29/00* (2006.01)
*G02B 21/26* (2006.01)

(52) U.S. Cl.
USPC ........... 362/300; 362/580; 362/581; 362/304; 362/305

(58) Field of Classification Search
USPC .......................... 362/580–581, 300, 304–305
See application file for complete search history.

(56) References Cited

U.S. PATENT DOCUMENTS

| | | | |
|---|---|---|---|
| 5,231,284 A | 7/1993 | Mizutani et al. | |
| 5,779,353 A * | 7/1998 | Kacheria | 362/293 |
| 6,071,001 A * | 6/2000 | Denuto et al. | 362/581 |
| 6,089,740 A * | 7/2000 | Forehand et al. | 362/573 |
| 6,217,205 B1 * | 4/2001 | Ward | 362/580 |
| 6,272,269 B1 * | 8/2001 | Naum | 385/43 |
| 6,628,868 B2 * | 9/2003 | Akira | 385/116 |
| 7,331,699 B2 | 2/2008 | Gawalkiewicz et al. | |
| 7,427,731 B2 * | 9/2008 | Gerhard et al. | 250/205 |
| 8,591,085 B2 * | 11/2013 | Nakabayashi et al. | 362/548 |
| 2008/0013178 A1 | 1/2008 | Terada | |
| 2008/0123342 A1 * | 5/2008 | Gluszczak et al. | 362/296 |

(Continued)

FOREIGN PATENT DOCUMENTS

| | | |
|---|---|---|
| JP | 05-018711 A | 1/1993 |
| JP | 10-068845 A | 3/1998 |

(Continued)

OTHER PUBLICATIONS

Japanese Office Action dated Nov. 26, 2013 issued in counterpart Japanese Application No. 2010-191774.

(Continued)

*Primary Examiner* — David J Makiya
(74) *Attorney, Agent, or Firm* — Holtz, Holtz, Goodman & Chick, PC

(57) ABSTRACT

A light source unit is equipped with a light source having a discharge lamp and a converging mirror, and a light guide formed of a liquid core fiber which is held by a light guide holding portion. The light source and the light guide are held in a casing made of a metal, and an infrared cut filter is provided in a cylindrical light shielding body surrounding an optical path in the interior of the casing. The light shielding body forms a stray light preventing member which prevents stray light from going out of the casing, and a light quantity adjusting member is provided between an opening of the light shielding body on a light guide side and a light incident port of the light guide. The light shielding body and the light guide holding portion are thermally insulated from each other by a heat insulating material portion.

6 Claims, 4 Drawing Sheets

(56) References Cited

FOREIGN PATENT DOCUMENTS

| | | |
|---|---|---|
| JP | 2000-057841 A | 2/2000 |
| JP | 2004-087423 A | 3/2004 |
| JP | 2008-020563 A | 1/2008 |
| JP | 2009-122468 A | 6/2009 |

OTHER PUBLICATIONS

Japanese Office Action dated Nov. 26, 2013 issued in counterpart Japanese Application No. 2010-211664.

* cited by examiner

LIGHT SOURCE UNIT

TECHNICAL FIELD

The present invention relates to a light source unit, more particularly to a light source unit used for supplying lighting light to, for example, a biomicroscope.

BACKGROUND ART

As a certain kind of light source unit used for supplying lighting light to, for example, an endoscope, has heretofore been mentioned a unit equipped with a light source 20 having a discharge lamp 21 and a converging mirror 25 converging light from the discharge lamp 21, and a light guide 52, on which the light from the light source 20 is incident, as illustrated in FIG. 5, and having a construction that these light source 20 and light guide 52 are held and fixed at respective predetermined positions in a casing 11, the light from the discharge lamp 21 reflected on the converging mirror 25 is struck on the light guide 52 by condensing the light at a condensing point located at an arrangement position of a light incident port 53 of the light guide 52, and the light is guided by this light guide 52 and emitted outside (see, for example, Patent Literature 1).

In the embodiment illustrated in this drawing, reference sign 40 is a light shielding body supported by a support 48 for light shielding body fixed to the casing 11 and surrounding an optical path L1 from the light source 20 to the light guide 52 of the light emitted from the discharge lamp 21 and converged by the converging mirror 25 and is also a stray light preventing member for preventing light toward other directions than the direction of the light incident port 53 of the light guide 52, which is generated in the interior of the casing 11, for example, light which travels on an optical path indicated by sign L2, from going out of the casing 11 as stray light. Reference sign 17 is a light quantity adjusting member for adjusting the quantity of the light incident on the light guide 52 and having a construction that a plurality of light passage apertures different in aperture diameter is formed in a fan-shaped light shielding plate 17A, and a light passage aperture 17B having an aperture diameter of a proper size is selected and located on the optical path.

CITATION LIST

Patent Literature

Patent Literature 1: U.S. Pat. No. 7,331,699 B2

SUMMARY OF INVENTION

Technical Problem

In the light source unit of such construction as described above, quartz fiber has heretofore been used as the light guide. However, sufficient flexural property is not achieved by the quartz fiber, and the total reflection angle of the quartz fiber is small, so that such a light source unit involves a problem that when the light guide is used in a flexed state, the illuminance of light emitted from the light guide becomes small. In addition, there is a demand for achieving a higher illuminance in the light source unit, so that it is considered to use a liquid core fiber with a light transmitting liquid filled into a flexible resin-made cladding to form a core by the light transmitting liquid in place of the quartz fiber.

According to the liquid core fiber, high flexural property is achieved compared with the quartz fiber, and the refractive index of the light transmitting liquid making up the core is higher than quartz glass, so that its total reflection angle is large, and its angular aperture (acceptance angle) is also large, and so such fiber can transmit light at a high efficiency to obtain high-illuminance light as outgoing light.

However, when the liquid core fiber is used as a light guide in the light source unit, there is a problem that light from a light source is not emitted from a light outgoing port of the light guide during its actuation.

The reason why such a problem is caused is that since infrared rays are included in the light emitted from the discharge lamp, and the light converged by the converging mirror is introduced into the liquid core fiber, the intensity of the infrared rays per unit sectional area in the liquid core fiber becomes high, and so the liquid making up the liquid core fiber is heated and boiled by the infrared rays, whereby the transmission of the light is prevented by bubbles produced in the interior of the liquid.

In view of the fact that it is difficult to remove the infrared rays in the light from the light source, specifically, that it is difficult to completely remove the infrared rays from the light emitted from the light source though the intensity of the infrared rays in the light from the light source can be weakened by transmitting the infrared rays of the light emitted from the discharge lamp through the converging mirror, the present inventors have carried out an investigation with a view toward preventing the infrared rays from being introduced into the liquid core fiber by providing an infrared cut filter on the optical path extending from the light source to the liquid core fiber.

However, it has been clarified that the heating of the liquid core fiber cannot be sufficiently inhibited according to the method of simply providing the infrared cut filter.

It has also been clarified that the following problems are caused when an infrared cut filter having a multi-layer reflection film is provided on the optical path extending from the light source to the liquid core fiber.

In short, in such a construction, the light emitted from the discharge lamp and converged by the converging mirror is applied to the infrared cut filter, and the transmitted light transmitted through this infrared cut filter is incident on the liquid core fiber. However, the light applied to the infrared cut filter includes not only light small in incident angle on the infrared cut filter, for example, perpendicularly incident light, but also light large in incident angle, for example, light which travels on an optical path indicated by sign L11. On the other hand, the infrared cut filter is high in incident angle dependence of light transmission property from the viewpoint of the structure of the multi-layer reflection film making up the infrared cut filter, so that the light transmission property, i.e., transmittance, greatly varies according to the incident angle of the light incident on the infrared cut filter. Specifically, transmitted light of the light large in incident angle on the infrared cut filter causes a wavelength shifting phenomenon that the spectral distribution thereof is shifted on a short wavelength side compared with transmitted light of the light small in incident angle. The following problems (a) and (b) are caused attending on the fact that the spectral distribution of the transmitted light of the light large in incident angle on the infrared cut filter is shifted on the short wavelength side as described above.

(a) The intensity of light on a long wavelength side in the light introduced into the liquid core fiber becomes small, so that the light source unit cannot be applied to uses utilizing the light on the long wavelength side.
(b) The light introduced into the liquid core fiber includes light on the short wavelength side, for example, light having a wavelength of 300 nm or less, so that there is a possibility that the liquid core fiber may be deteriorated or broken because that deteriorated by irradiation of the light having the wavelength of 300 nm or less, for example, a resin forming a cladding, is used as a member making up the liquid core fiber.

In addition, there has been a demand for miniaturizing the light source unit in recent years. When a clearance between the light source and the liquid core fiber is made short in order to meet such a demand, the incident angle of the light from the light source on the liquid core fiber naturally becomes large because there is need to condense the light from the light source at a light incident port of the liquid core fiber because of its structure. When composition that the infrared cut filter is arranged between the light source and the liquid core fiber in the light source unit miniaturized by making the clearance between the light source and the liquid core fiber short as described above is adopted, light larger in incident angle is unavoidably incident on the infrared cut filter, so that the above-described problems (a) and (b) become marked.

The present invention has been made on the basis of the foregoing circumstances and has as its object the provision of a light source unit of a construction using a liquid core fiber as a light guide, by which the liquid core fiber making up a light guide can be inhibited from being overheated, thereby supplying light without causing evils attributed to the overheating of the liquid core fiber.

Another object of the present invention is to provide a light source unit of a construction using a liquid core fiber as a light guide, by which an infrared cut filter having a multi-layer reflection film can prevent infrared rays from being introduced into the liquid core fiber to prevent the liquid core fiber from being heated, and its miniaturization can be made without causing evils.

Solution to Problem

A light source unit according to the present invention comprises a light source having a discharge lamp and a converging mirror converging light from the discharge lamp, and a light guide, on which the light from the light source is incident, wherein the light guide is formed of a liquid core fiber with a light transmitting liquid filled into a cladding, the light source and the light guide are held by a light source holding portion and a light guide holding portion, respectively, in a casing made of a metal, said casing being equipped with a cylindrical light shielding body supported by a support for light shielding body fixed to the casing and surrounding an optical path extending from the light source to the light guide in the interior of the casing, an infrared cut filter is provided in the light shielding body so as to be located on the optical path from the light source to the light guide, and a heat insulating material portion formed of a heat insulating material is interposed between the light shielding body and the light guide holding portion in the support for light shielding body and the casing, whereby the light shielding body and the light guide holding portion are thermally insulated from each other.

In the light source unit, the support for light shielding body may preferably be formed of a heat insulating material. This heat insulating material may preferably have a heat conductivity of 3 [$W \cdot m^{-1} \cdot K^{-1}$] or less.

In the light source unit, a cooling air inlet and a cooling air outlet may preferably be provided in the casing to cool the light shielding body by cooling air from a cooling fan.

A light source unit according to the present invention comprises a light source having a discharge lamp and a concave mirror receiving light from the discharge lamp and projecting parallel light or substantially parallel light, and a light guide, on which the light from the light source is incident, wherein the light guide is formed of a liquid core fiber with a light transmitting liquid filled into a cladding, and wherein an infrared cut filter having an infrared reflecting layer formed of a multi-layer reflection film is provided on an optical path along which the projected light from the concave mirror reaches a light incident port of the light guide, and a condenser lens is provided so as to be located farther onward in a traveling direction of the light in the optical path than the infrared cut filter.

In the light source unit, it may be preferable that the concave mirror is composed of a spheroidal mirror, the first focal point thereof is located at a luminescent spot of the discharge lamp, and the second focal point thereof is located with a space in a direction more separating from the first focal point than an arrangement position of the light incident port of the light guide, and that the focal point of the condenser lens is located with a space in a direction more separating from the first focal point of the concave mirror than the arrangement position of the light incident port of the light guide.

In the light source unit, the maximum incident angle of the light incident on the infrared out filter may preferably be at most 15°.

Advantageous Effects of Invention

In the light source unit according to the present invention, the liquid core fiber is used as the light guide, the infrared cut filter is provided, and the heat insulating material portion formed of the heat insulating material is interposed between the light shielding body and the light guide holding portion, whereby the light shielding body and the light guide holding portion are thermally insulated from each other, so that infrared rays are inhibited from being struck on the liquid core fiber making up the light guide to inhibit the liquid core fiber from being heated by the infrared rays. In addition, even when the light shielding body is heated to a high temperature by receiving the light from the light source, the heat of the light shielding body is inhibited from being transmitted to the light guide holding portion by transmitting the heat through the members making up this light source unit, so that the light guide can be inhibited from being heated by the light shielding body heated to the high temperature.

Accordingly, according to the light source unit of the present invention, the liquid core fiber making up the light guide can be inhibited from being overheated when the liquid core fiber is used as the light guide, thereby supplying light without causing evils attributed to the overheating of the liquid core fiber.

In the light source unit according to the present invention, the support for light shielding body is formed of the heat insulating material, whereby the support for light shielding body has an action that the light shielding body and the light guide holding portion are thermally insulated from each other in addition to the action that the light shielding body is supported and fixed to the casing, so that the heat of the light shielding body is inhibited from being transferred to the casing through the member supporting the light shielding body. Accordingly, there is no need to separately provide an exclusive member for supporting the light shielding body and an exclusive member for thermally insulating the light shielding body and the light guide holding portion in the casing from each other, so that a high degree of freedom of design is obtained.

In the light source unit according to the present invention, the cooling air inlet and the cooling air outlet are provided in the casing to cool the light shielding body by cooling air from the cooling fan, thereby inhibiting the light shielding body receiving the light from the light source from raising its temperature, so that the liquid core fiber can be still more surely inhibited from being overheated.

In the light source unit according to the present invention, the infrared cut filter is provided, whereby infrared rays are inhibited from being struck on the liquid core fiber making up the light guide to inhibit the liquid core fiber from being heated due to the incidence of the infrared rays. In addition, the unit is so constructed that parallel light or substantially parallel light is projected from the concave mirror of the light source, and the condenser lens is provided, so that even when the infrared cut filter has the infrared reflecting layer formed of the multi-layer reflection film, and transmitted light of the light struck at a large incident angle causes a wavelength shift that the spectral distribution thereof is shifted on a short wavelength side because of its structure, the concave mirror inhibits the light large in incident angle from being struck on the infrared cut filter. In addition, since the light high in degree of parallelization is condensed by the condenser lens, the light is incident on the light guide at a high efficiency, and thus the occurrence of the evils attributed to the use of the infrared cut filter equipped with the multi-layer reflection film can be inhibited. After all, when the liquid core fiber is used as the light guide, the liquid core fiber making up the light guide can be inhibited from being heated due to the irradiation of the infrared rays without causing any evil.

Further, the spheroidal mirror is used as the concave mirror, whereby there is no need to make the aperture of the concave mirror large for obtaining high light intensity in outgoing light from the light guide because this spheroidal mirror can converge the light emitted from the discharge lamp at a high efficiency and project the light high in degree of parallelization, so that a high degree of freedom of design can be obtained to easily miniaturize the unit.

DESCRIPTION OF EMBODIMENTS

The first embodiment of the present invention will hereinafter be described.

Figure 1:
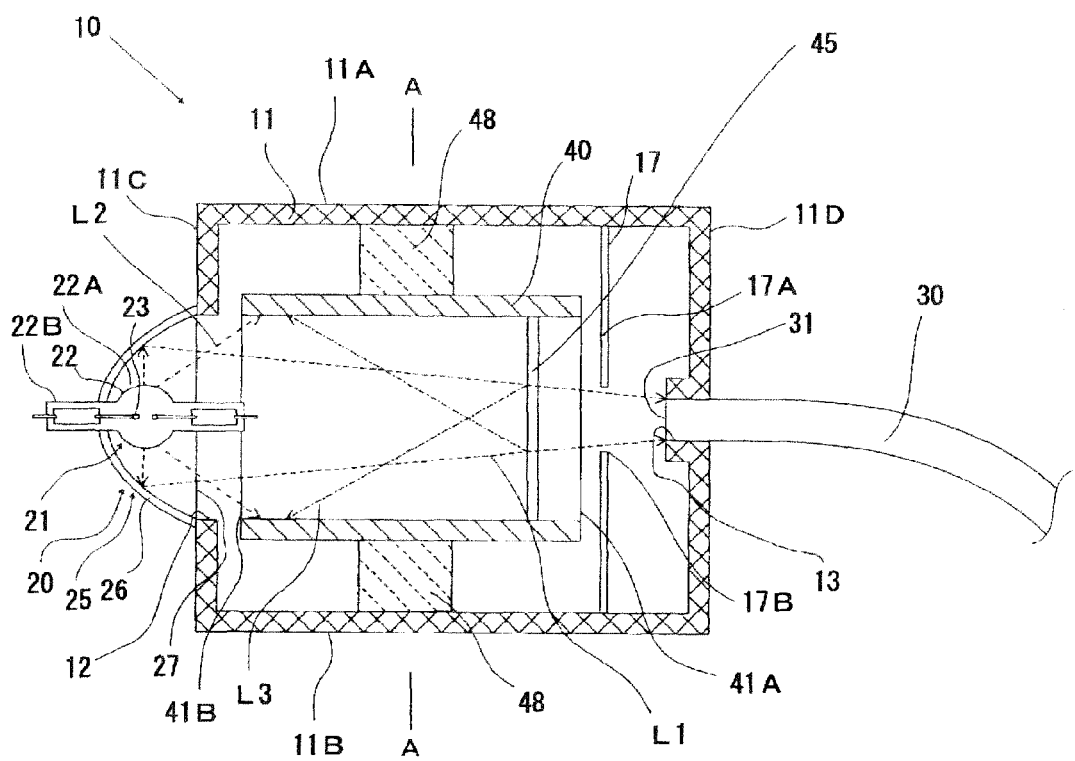
FIG. 1 is an explanatory cross-sectional view illustrating a light source unit according to a first embodiment of the present invention.
Figure 2:
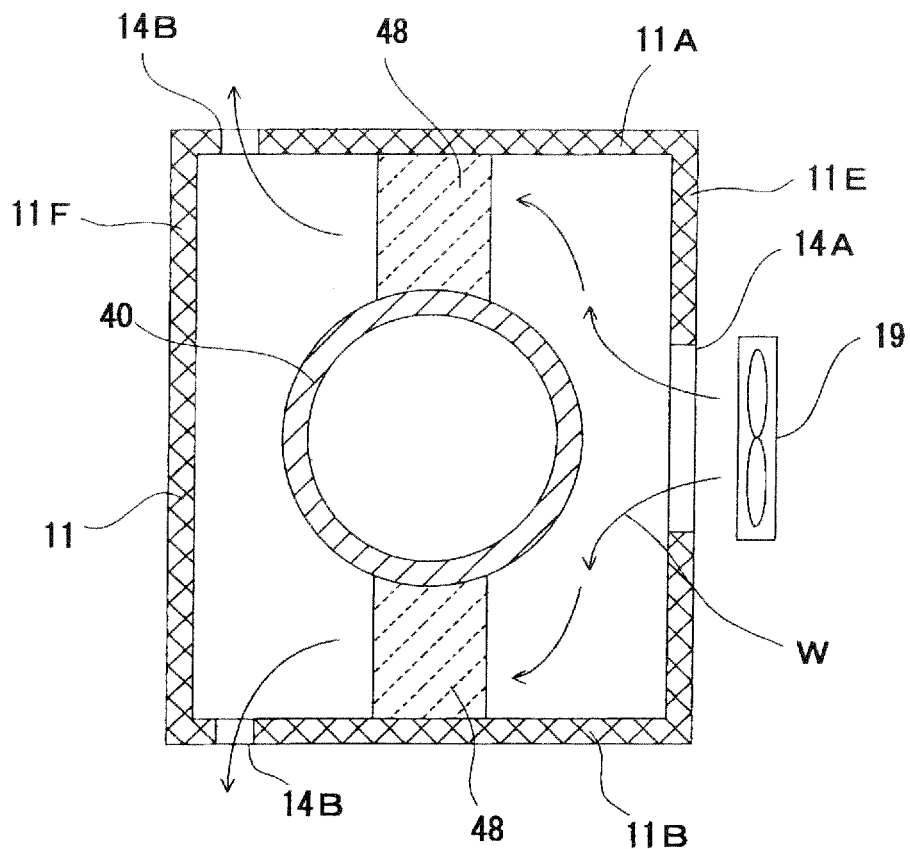
FIG. 2 is a cross-sectional view taken along line A-A in FIG. 1.

FIG. 1 is an explanatory cross-sectional view illustrating a light source unit according to the first embodiment of the present invention, and FIG. 2 is a cross-sectional view taken along line A-A in FIG. 1.

This light source unit 10 has a construction that a light source 20 having a discharge lamp 21 and a converging mirror 25 converging light from the discharge lamp 21, and a light guide 30, on which the light from the light source is incident, are held by a casing 11 having an appearance form of a rectangular parallelopiped and formed of, for example, a metal such as aluminum or stainless steel, and the light from the light source 20 is emitted outside through the light guide 30.

In the casing 11, a discharge lamp holding portion 12 having an opening conforming to a light projecting port formed of an aperture 27 of the converging mirror 25 is formed in a side wall portion 11C on one end side (left end side in FIG. 1), and a light guide holding portion 13 formed of a cylindrical portion having an inner peripheral surface of an internal diameter conforming to an external diameter of a light incident port 31 of the light guide 30 is formed in a side wall portion 11D on the other end side (right end side in FIG. 1), which is opposite to the side wall portion 11C on said one end side, whereby the light source 20 and the light guide 30 are fixed in such a manner that the light projecting port in the light source 20 and the light incident port 31 of the light guide 30 are opposite to each other in the interior of the casing 11. In addition, a cylindrical light shielding body 40 is supported by a support 48 for light shield body and provided in the interior of the casing 11 so as to surround an optical path L1 from the light source 20 to the light guide 30.

In this embodiment illustrated, in the interior of the casing 11, a light quantity adjusting member 17 for adjusting the quantity of the light incident on the light incident port 31 of the light guide 30 is provided at a position between an opening 41A of the light shielding body 40 on a light guide side and the light incident port 31. This light quantity adjusting member 17 has a construction that a plurality of light passage apertures different in aperture diameter is formed in a fan-shaped light shielding plate 17A, and a light passage aperture 17B having an aperture diameter of a proper size is selected and located on the optical path.

The light source 20 equipped with, as the discharge lamp 21, an extra-high pressure discharge lamp energized and lit by, for example, a direct-current power supply. The converging mirror 25 furnishes a rotary reflecting surface arranged so that its central axis is coincident with an arc direction of this discharge lamp 21. The condensing point or focal point thereof is arranged, for example, on the light incident port 31 of the light guide 30 or in vicinity of the light incident port 31 such as in a position located at interior of the light guide 30 farther onward in the traveling direction of the light than the light incident port 31.

The discharge lamp 21 is equipped with a light emitting portion 22A having a substantially spherical external form, in the interior of which a discharge space is formed, and a light emitting tube 22 made up of rod-like sealing portions 22B formed integrally with both ends of the light emitting portion 22A and each extending outward along a direction of a tube axis of the light emitting tube 22 and composed of, for example, quartz glass, and in the interior of the light emitting portion 22A, a pair of electrodes 23 are arranged so as to be opposite to each other along the direction of the tube axis of the light emitting tube 22, and an enclosure is sealed.

Here, examples of the enclosure in the discharge lamp 21 include 0.05 mg/mm$^3$ of mercury, rare gasses such as, for example, argon, and halogens such as, for example iodine, bromine and chlorine. When a metal halide lamp is constructed, a metal such as gallium or iron is sealed in addition to such an enclosure. The rare gas is sealed for improving lighting startability, and its charged pressure is, for example, 13 kPa in terms of a static pressure. The halogen is sealed in the form of a compound with mercury or any other metal for forming a halogen cycle within the light emitting portion 22A, thereby inhibiting an electrode substance from adhering to an inner wall of the light emitting portion 22A.

The converging mirror 25 is composed of, for example, borosilicate glass or crystallized glass and has a light converging portion 26 equipped with a concave converging and reflecting surface. At a front end of this light converging portion 26, an aperture 27 forming a light projecting port of a circular form viewed from the front is formed. On an inner surface of this light converging portion 26, is formed, as the converging and reflecting surface, a reflection film which reflects light within a necessary wavelength range of light emitted from the discharge lamp 21 and transmits light within an unnecessary wavelength range behind the converging mirror 25.

Figure 3:
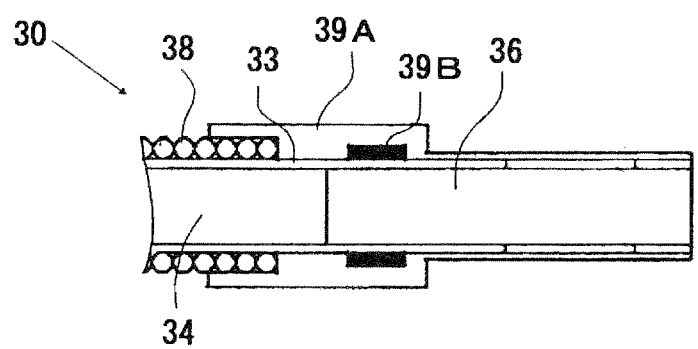
FIG. 3 is an explanatory cross-sectional view illustrating the construction of a liquid core fiber making up the light source unit in FIG. 1.

As the light guide 30, is used a liquid core fiber with a light transmitting liquid 34 filled into a cladding 33 as illustrated in FIG. 3 to form a core by this light transmitting liquid 34.

In this liquid core fiber, the cladding 33 is a flexible tube formed of a resin such as, for example, polytetrafluoroethylene, and both ends of this cladding 33 are sealed by a sealing stopper composed of a quartz glass-made rod 36 or the like. The light incident port 31 and an light outgoing port (not illustrated) are formed at a proximal end portion sealed by such a stopper and a distal end portion, respectively.

In the embodiment in FIG. 3, an optical path for guiding the light from the light source 20 by the quartz glass-made rod 36 provided at both ends and the light transmitting liquid 34 in the liquid core fiber, and the cladding 33 is provided so as to surround the outer peripheries of these rods 36 and light transmitting liquid 34. A flexible metal sheath 38 is provided on the outer peripheral surface of the cladding 33 at a portion surrounding the light transmitting liquid 34, whereby flexibility owing to the light transmitting liquid 34 is ensured in a region between the rods 36 of the liquid core fiber, and the flexibility is retained by the flexible metal sheath 38. In addition, in the outer peripheral surface of the cladding 33, a load is applied at boundary portions between the light transmitting liquid 34 and the rods 36 due to the flexibility brought by being furnished with the light transmitting liquid 34, so that a metal ferrule 39A is provided through a gasket 39B provided on a portion surrounding the rod 36 in a region about the boundary between the light transmitting liquid 34 and the rod 36, thereby forming a reinforced structure.

The light shielding body 40 is provided as a stray light preventing member for preventing stray light, which is generated in the interior of the casing 11, from going out of the casing 11, and is a cylindrical body formed of, for example, a metal such as aluminum or stainless steel, having an internal diameter conforming to the light projecting port in the light source 20 so as to surround the optical path L1 from the light source 20 to the light guide 30 and arranged in such a manner that one opening 41B is opposite to the light projecting port in the light source 20, and the other opening 41A is opposite to the light incident port 31 of the light guide 30.

In the embodiment of this drawing, the light shielding body 40 is provided so as to extend in the direction of an optical axis of the converging mirror in a region between the light projecting port in the light source 20 and the light quantity adjusting member 17.

Here, the stray light generated in the casing 11 means light which is not struck on the light guide 30, such as, for example, light directly emitted from the discharge lamp 21 without being reflected on the converging mirror 25 of the light projected from the light projecting port in the light source 20, for example, light which travels on an optical path indicated by L2 in FIG. 1, or light reflected on an infrared cut filter 45, which will be described subsequently, for example, light which travels on an optical path indicated by L3 in FIG. 1.

The infrared cut filter 45 is provided in the light shielding body 40 so as to be located on the optical path L1 from the light source 20 to the light guide 30.

In the embodiment of this drawing, the infrared cut filter 45 is fixed with the peripheral edge portion thereof held by the internal periphery of the slight shielding body 40 and is provided in a state the internal space of the light shielding body 40 is divided in an axial direction (lateral or horizontal direction in FIG. 1) of the light shielding body 40.

The infrared cut filter 45 is preferably arranged at a position approaching the light incident port 31 of the light guide 30, specifically, a position approaching the opening 41A opposite to the light guide 30 in an extending direction of the light shielding body 40.

The infrared cut filter 45 is provided at the position approaching the light incident port 31 of the light guide 30, whereby the light shielding body can prevent light reflected on the infrared cut filter 45, i.e., stray light originated from infrared rays, from going out of the casing 11.

The infrared cut filter 45 is formed by providing an infrared reflecting layer on the surface of, for example, a transparent substrate, and infrared rays are reflected by this infrared reflecting layer, thereby preventing or inhibiting the transmission of the infrared rays. As the infrared reflecting layer, may be used, for example, a multi-layer reflection film obtained by successively laminating, for example, titanium oxide ($TiO_2$) and silica ($SiO_2$) on the transparent substrate by a vapor deposition method.

The infrared cut filter 45 is only required to have at least properties that an infrared transmission rate is low, and a transmission rate of light making up lighting light such as visible light and having a wavelength of 340 to 700 nm is high. For example, both infrared transmission rate and ultraviolet transmission rate may be low.

The support 48 for light shielding body is in the form of, for example, a column itself fixed to the casing 11, and an proximal end portion thereof is fixed to the casing 11, and the light shielding body 40 is fixed to a distal end portion thereof, whereby the light shielding body 40 is supported at a predetermined position in the interior of the casing 11.

In the embodiment of this drawing, the light shielding body 40 is supported by two supports 48 for light shielding body respectively fixed to a top portion 11A (upper surface in FIG. 1) and a bottom portion 11B (lower surface in FIG. 1), which are opposite to each other in the casing 11, at a central region in an axial direction on its outer peripheral surface. The two supports for light shielding body are fixed to the top portion 11A and the bottom portion 11B, respectively, by screwing, and the light shielding body 40 is fixed to these two supports for light shielding body by screwing.

In this embodiment, the support 48 for light shielding body is formed of a heat insulating material. In short, the support 48 for light shielding body acts as a supporting member for supporting and fixing the light shielding body 40 and also acts as a heat insulating member for thermally insulating the light shielding body 40 and the light guide holding portion 13 in the casing 11 from each other.

Here, the heat insulating material is lower in heat conductivity than the material forming the casing 11. For example, the heat conductivity value thereof is preferably less than ⅕ times of the heat conductivity of the material forming the casing 11. Specifically, the heat conductivity is preferably 3 [W·m⁻¹·K⁻¹] or less.

The heat conductivity of the heat insulating material is 3 [W·m⁻¹·K⁻¹] or less, whereby the heat conductivity of the heat insulating member becomes extremely low compared with the metal such as aluminum or stainless steel, which forms the casing 11, so that even when the light shielding body 40 is heated to a high temperature by the light from the light source 20, the heat insulating material portion formed by the heat insulating material (support 48 for light shielding body in the illustrated embodiment), which is interposed between the light shielding body 40 and the light guide holding portion 13 surely creates a state that the light shielding body 40 and the light guide holding portion 13 have been thermally insulated from each other, thereby sufficiently inhibiting the liquid core fiber from being heated by the heat of the light shielding body 40 transmitted to the light guide holding portion 13 through the members making up the light source unit 10, specifically, the casing 11 and the support 48 for light shielding body.

Incidentally, the heat conductivity of aluminum is 138 [W·m⁻¹·K⁻¹], and the heat conductivity of stainless steel is 16 [W·m⁻¹·K⁻¹].

Specific examples of the heat insulating material include ceramics such as steatite (MgO.SiO₂) and resins such as polyacetal (POM).

Incidentally, the heat conductivity of steatite is 2 to 3 [W·m⁻¹·K⁻¹], and the heat conductivity of polyacetal is 0.25 [W·m⁻¹·K⁻¹].

The light source unit 10 preferably has a construction that a cooling air inlet 14A and a cooling air outlets 14B are provided in the casing 11 as illustrated in FIG. 2 to cool the light shielding body 40 by cooling air from a cooling fan 19.

In the casing 11, the cooling air inlet 14A and the cooling air outlets 14B are preferably provided in regions opposite to an outer peripheral surface of the light shielding body 40 in surfaces forming the casing 11, which are parallel to an axial direction of the light shielding body 40, and are also preferably provided in component plates different from each other.

The cooling air inlet 14A and the cooling air outlets 14B are formed in regions opposite to the outer peripheral surface of the light shielding body 40 in the component plates different from each other, whereby the cooling air W from the cooling fan 19 is directly blown against the outer peripheral surface of the light shielding body 40 as indicated by arrows in FIG. 2, and then circulated along a peripheral direction around the outer peripheral surface of the light shielding body 40, so that the light shielding body 40 can be cooled at a high efficiency. In addition, the cooling air outlets 14B are formed in other component plates than a component plate (specifically, a side wall portion 11D) in which the light guide holding portion 13 has been formed, thereby inhibiting the cooling air, which has received heat from the light shielding body 40 and the like by circulating in the interior of the casing 11, from flowing toward the light incident port 31 of the light guide 30, so that the light guide 30 can be inhibited from being heated by the cooling air which has received such heat.

In the illustrated embodiment, the cooling air inlet 14A is provided at a central portion in a region opposite to the outer peripheral surface of the light shielding body 40 in one side wall portion 11E of a pair of side wall portions continuous with the top portion 11A and the bottom portion 11B to which the supports 48 for light shielding body, and the two cooling air outlets 14B are provided in respective portions approaching boundaries with the side wall portion 11F opposite to the side wall portion 11E, in which the cooling air inlet 14A is provided, in regions opposite to the outer peripheral surface of the light shielding body 40 of the top portion 11A and the bottom portion 11B. The cooling fan 19 is opposite to the cooling air inlet 14A and provided in contiguity with the cooling air inlet 14A.

As the cooling fan 19, any fan may be used so far as it can supply cooling air to the interior of the casing 11 through the cooling air inlet 14A and cause the cooling air to circulate in the interior of the casing 11.

The flow rate of the cooling air supplied to the interior of the casing 11 by the cooling fan 19 is, for example, 0.8 [m³/min].

In the light source unit 10 of such construction, the discharge lamp 21 making up the light source 20 is lit, whereby light from the discharge lamp 21 is reflected on the converging mirror 25 and converged, thereby being projected from the light projecting port, this light from the light source 20 passes through the interior of the light shielding body 40 and is incident on the light guide 30 from the light incident port 31 through the light quantity adjusting member 17, and this light incident on the light guide 30 is guided by the light guide 30, thereby being emitted from the light outgoing port.

In the light source unit 10, the infrared cut filter 45 is provided, so that infrared rays of the light from the light source 20 are reflected by the infrared cut filter 45 in the process that the light pass through the interior of the light shielding body 40, to inhibit the infrared rays from being struck on the liquid core fiber making up the light guide 30, thereby inhibiting the liquid core fiber from being heated by the infrared rays.

In the light source unit 10, the light shielding body 40 is heated to a high temperature by receiving stray light composed of light which is not struck on the light guide 30, such as, for example, light directly emitted from the discharge lamp 21 without being reflected on the converging mirror 25 of the light projected from the light projecting port in the light source 20, or light reflected on the infrared cut filter 45. However, the heat insulating material portion formed by the support 48 for light shielding body formed of the heat insulating material is interposed between the light shielding body 40 and the light guide holding portion 13 in the support 48 for light shielding body and the casing 11, whereby the light shielding body 40 and the light guide holding portion 13 are thermally insulated from each other, so that the heat of the light shielding body 40 is inhibited from being transmitted to the light guide holding portion 13 by transmitting the heat through the members making up this light source unit 10, specifically, the support 48 for light shielding body and the casing 11 even when the light shielding body 40 is heated to the heat temperature. Thus, the liquid core fiber making up the light guide 30 can be inhibited from being heated through this light guide holding portion 13 by the light shielding body 40 heated to the high temperature.

In the light source unit 10, the cooling air is supplied to the interior of the casing 11 through the cooling air inlet 14A from the cooling fan 19 in a state that the discharge lamp 21 making up the light source 20 has been lit, this cooling air supplied from the cooling air inlet 14A is blown against the outer peripheral surface of the light shielding body 40, passed through the support 48 for light shielding body while circulating along a peripheral direction around the outer peripheral surface of the light shielding body 40, and discharged outside the casing 11 from the cooling air outlet 14B. In this manner, the cooling air is circulated in the interior of the casing 11 so as to flow along the outer peripheral surface of the light shielding body 40, thereby cooling the light shielding body 40, the support 48 for light shielding body and the casing 11. Therefore, the light shielding body 40 receiving the light from the light source 20 is inhibited from increasing in temperature, and also the liquid core fiber making up the light guide 30 can be still more surely inhibited from being overheated because the support 48 for light shielding body and the casing 11 are also cooled collectively.

As described above, according to the light source unit 10, the liquid core fiber making up the light guide 30 is inhibited from being overheated, so that the light can be supplied by using the excellent optical properties that the liquid core fiber has without involving evils caused by heating the liquid core fiber, such as, for example, a phenomenon that the light from the light source 20 is not emitted from the light outgoing port of the light guide 30 during actuation, or a phenomenon that the light transmitting liquid of the liquid core fiber making up the light guide 30 is deteriorated.

In the light source unit 10, the support 48 for light shielding body is formed of the heat insulating material, whereby the support 48 for light shielding body has an action that the light shielding body 40 and the light guide holding portion 13 are thermally insulated from each other in addition to an action that the light shielding body 40 is supported and fixed to the casing 11, so that it can be inhibited that the heat of the light shielding body 40 is transmitted to the casing 11 through the support 48 for light shielding body supporting the light shielding body 40. Accordingly, there is no need to separately provide an exclusive member for supporting the light shielding body 40 and an exclusive member for thermally insulating the light shielding body 40 and the light guide holding portion 13 in the casing 13 from each other, so that a high degree of freedom of design is obtained.

In the light source unit according to the first embodiment of the present invention, various changes or modifications may be added without being limited to the above-described embodiments.

For example, the heat insulating material portion formed of the heat insulating material interposed between the light shielding body and the light guide holding portion is preferably formed by the support for light shielding body from the viewpoint of the degree of freedom of design. However, this heat insulating material portion may be provided separately from the support for light shielding body. Specifically, for example, a portion to which the support for light shielding body is fixed, or a part of the casing, such as the light guide holding portion, may be formed by the heat insulating material.

In addition, the light source unit is preferably so constructed that the cooling air inlet and the cooling air outlets are provided in the casing, and the light shielding body is cooled by cooling air from the cooling fan like the above embodiment from the viewpoint of more effectively inhibiting the liquid core fiber from being heated by the heat of the light shielding body. However, the unit may have a construction that the cooling air is not supplied to the interior of the casing.

Experimental Examples that were conducted for confirming actions and effects in the first embodiment of the present invention will hereinafter be described.

Experimental Example 1

An light source unit (hereinafter also referred to as "light source unit (1)") having the construction illustrated in FIG. 1 and FIG. 2 was fabricated.

A light source making up this light source unit (1) is composed of an extra-high pressure mercury lamp whose rated power consumption is 130 W and a converging mirror reflecting and converging light within a wavelength range up to 800 nm, and its maximum incident angle of light at a focal point is 13.5°.

As a light guide, was used a liquid core fiber manufactured by LUMATEC CO.

A casing is made of aluminum (heat conductivity: 138 [W·m$^{-1}$·K$^{-1}$]), and the light source and the light guide are supported by this casing in such a manner that a clearance between them, i.e., a clearance between a light projecting port in the light source and a light incident port in the light guide is 100 mm.

A light shielding body is made of aluminum, and as an infrared cut filter, was used a filter that transmits light having a wavelength of 360 to 700 nm and reflects light in any other wavelength range than the above range.

A support for light shielding body is made of polyacetal (heat conductivity: 0.25 [W·m$^{-1}$·K$^{-1}$]).

The light source unit (1) fabricated was actuated under conditions of 40° C. in temperature to measure a temperature of the light incident port of the light guide after 8 hours elapsed from the beginning of the actuation. A result is shown in Table 1.

In the light source unit (1), a cooling fan was actuated during the lighting of the discharge lamp under conditions that the flow rate of cooling air supplied to the interior of the casing is 0.8 [m$^3$/min].

A surface temperature of the casing was also measured after 8 hours elapsed from the beginning of the actuation. As a result, the temperature was 50° C.

Experimental Example 2

An light source unit (hereinafter also referred to as "light source unit (2)") having the same construction as in the light source unit (1) according to Experimental Example 1 except that no cooling fan was used was fabricated, and regarding the light source unit (2) fabricated, a temperature of the light incident port of the light guide was measured after 8 hours elapsed from the beginning of the actuation in the same manner as in Experimental Example 1. A result is shown in Table 1.

Comparative Experimental Example 1

An light source unit (hereinafter also referred to as "comparative light source unit (1)") having the same construction as in the light source unit (2) according to Experimental Example 2 except that the support for light shielding body was formed by using aluminum in place of polyacetal was fabricated, and regarding the comparative light source unit (1) fabricated, a temperature of the light incident port of the light guide was measured after 8 hours elapsed from the beginning of the actuation in the same manner as in Experimental Example 1. A result is shown in Table 1.

A surface temperature of the casing was also measured after 8 hours elapsed from the beginning of the actuation. As a result, the temperature was 75° C.

Comparative Experimental Example 2

An light source unit (hereinafter also referred to as "comparative light source unit (2)") having the same construction as in the light source unit (2) according to Experimental Example 2 except that no infrared cut filter was provided, and the support for light shielding body was formed by using aluminum in place of polyacetal was fabricated, and regarding the comparative light source unit (2) fabricated, a temperature of the light incident port of the light guide was measured after 8 hours elapsed from the beginning of the actuation in the same manner as in Experimental Example 1. A result is shown in Table 1.

TABLE 1

|  | Material of Support for light shielding body | Existence of Infrared cut filter | Existence of Cooling fan | Temperature of Light incident port of Light guide |
|---|---|---|---|---|
| Experimental Example 1 | Polyacetal | exist | exist | 80° C. |
| Experimental Example 2 | Polyacetal | exist | none | 120° C. |
| Comparative Experimental Example 1 | Aluminum | exist | none | 150° C. or higher |
| Comparative Experimental Example 2 | Aluminum | none | none | 190° C. or higher |

From the results shown in Table 1, it was confirmed that according to the light source unit (1) and light source unit (2) of the present invention, the support for light shielding body is formed by polyacetal (heat insulating material), and the infrared cut filter is provided, so that the liquid core fiber is not heated to a temperature exceeding the withstanding temperature (about 130° C.) thereof even after 8 hours elapsed from the beginning of the actuation, and the liquid core fiber can be inhibited from being overheated.

In the light source unit (1), it was also confirmed that the cooling air is circulated in the interior of the casing to cool the light shielding body, whereby the liquid core fiber can be still more effectively inhibited from being heated by the heat of the light shielding body.

On the other hand, in the comparative light source unit (1) and comparative light source unit (2), it was confirmed that the support for light shielding body is formed by the same aluminum as the material forming the casing, and no heat insulating material portion is interposed between the light shielding body and the light guide holding portion, so that the temperature of the light incident port of the light guide is raised to at least 150° C. In particular, in the comparative light source unit (2), it was confirmed that the temperature of the light incident port of the light guide is raised to at least 190° C. because no infrared cut filter is provided.

Here, the reason why the temperature of the light incident port of the light guide in the comparative light source unit (1) is raised to at least 150° C. though the infrared cut filter is provided, and so infrared rays are not struck on the liquid core fiber making up the light guide is presumed to be as follows.

In short, it is presumed that in the comparative light source unit (1), the light shielding body is heated by infrared rays reflected on the infrared cut filter, and the heat of the light shielding body is transmitted to the light guide holding portion through the support for light shielding body and the casing to heat this light guide holding portion to a high temperature, and so the light guide is overheated.

Figure 4:
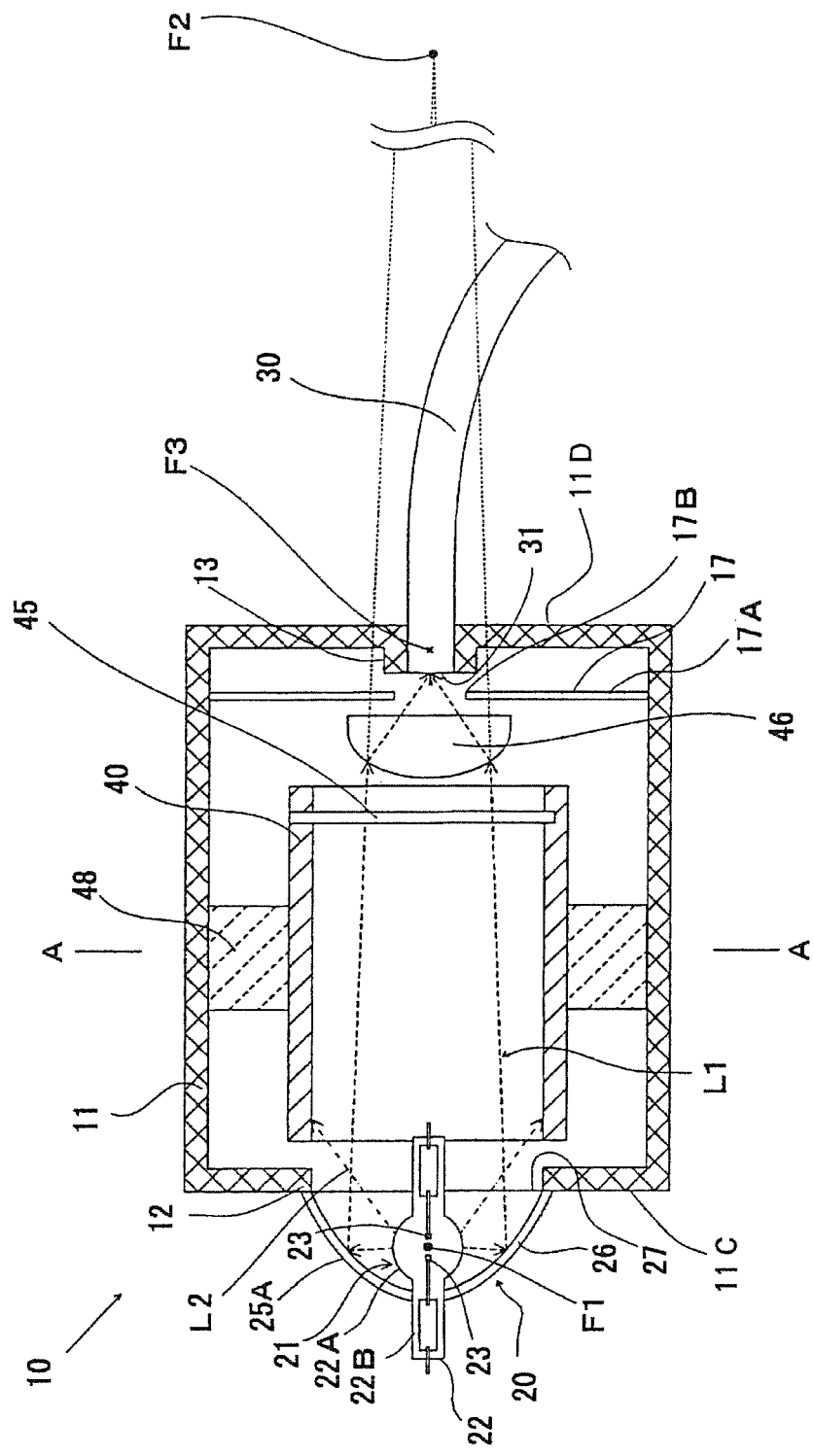
FIG. 4 is an explanatory cross-sectional view illustrating a light source unit according to a second embodiment of the present invention.
Figure 5:
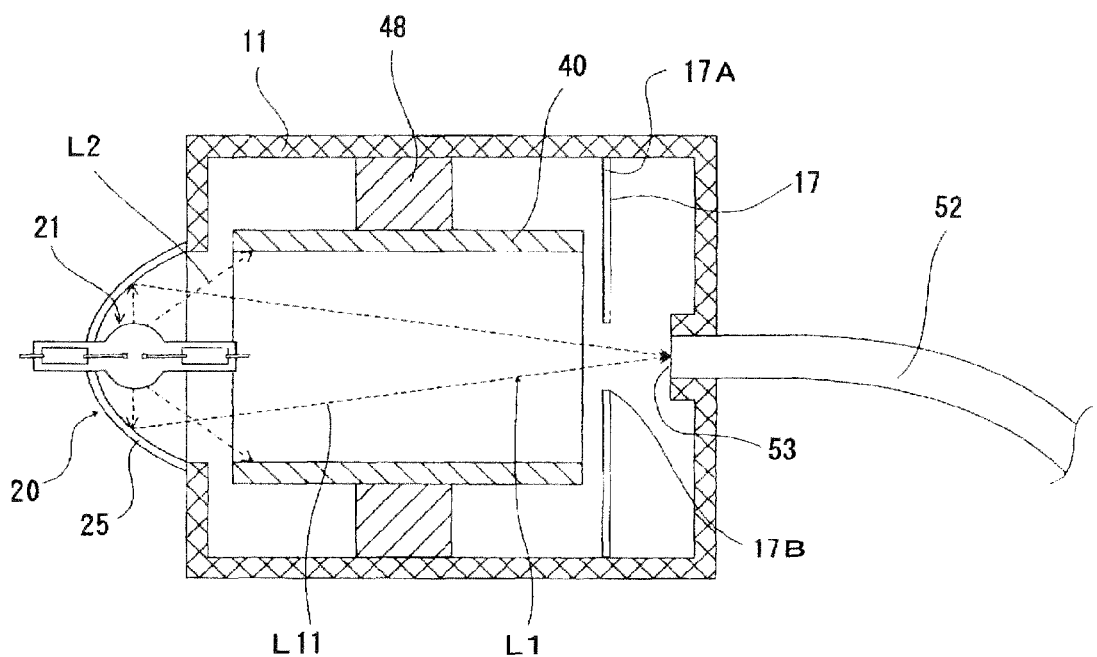
FIG. 5 is an explanatory cross-sectional view illustrating an exemplary construction of a conventional light source unit.

FIG. 4 is an explanatory cross-sectional view illustrating a light source unit according to the second embodiment of the present invention.

Like the first embodiment, this light source unit 10 has a construction that a light source 20 having a discharge lamp 21 and a concave mirror 25A arranged so as to surround the discharge lamp 21 and projecting light emitted from the discharge lamp 21 forward, and a light guide 30, on which the projected light from the concave mirror 25A making up the light source 20 is incident, are held by a casing 11 having an appearance form of a rectangular parallelopiped and formed of, for example, a metal such as aluminum or stainless steel, and the projected light from the concave mirror 25A is emitted outside through the light guide 30.

In the casing 11, a discharge lamp holding portion 12 having an opening conforming to a light projecting port formed of an aperture 27 of the concave mirror 25A in the light source 20 is formed in a side wall portion 11C on one end side, and a light guide holding portion 13 formed of a cylindrical portion having an internal diameter conforming to an external diameter of the light guide 30 is formed in a side wall portion 11D on the other end side, which is opposite to the side wall portion 11C on said one end side, whereby the light source 20 and the light guide 30 are fixed in such a manner that the light projecting port in the light source 20 and the light incident port 31 of the light guide 30 are opposite to each other in the interior of the casing 11. In addition, a cylindrical light shielding body 40 as a stray light-preventing member is supported by a support 48 for light shield body fixed to the casing 11 and arranged in the interior of the casing 11 so as to surround an optical path L1 from the concave mirror 25A to the light guide 30.

In this embodiment, an infrared cut filter 45 and a condenser lens 46 are provided on the optical path L1 from the concave mirror 25A to the light guide 30.

The concave mirror 25A in this embodiment receives and reflects light emitted from the discharge lamp 21, and projects light high in degree of parallelization composed of parallel light or substantially parallel light of that light is projected as projected light from the light projecting port formed by the aperture 27.

Here, "light high in degree of parallelization" in this description means light having an incident angle of at most 15° on the infrared cut filter 45.

This concave mirror 25A is composed of, for example, borosilicate glass or crystallized glass and has a light reflection portion 26 equipped with a concave reflection surface. At a front end of this light reflection portion 26, the aperture 27 forming a light projecting port of a circular form viewed from the front is formed. On an inner surface of the light reflection portion 26, is formed, as the reflection surface, a reflection film which reflects light within a necessary wavelength range of light emitted form the discharge lamp 21 and transmits light within an unnecessary wavelength range behind the concave mirror 25A.

As the concave mirror 25A, is preferably used a spheroidal mirror. This spheroidal mirror is arranged in such a manner that the first focal point F1 thereof is located at a luminescent spot of the discharge lamp 21, and the second focal point F2 thereof is located with a space in a direction more separating from the first focal point F1 than an arrangement position of the light incident port 31 of the light guide 30 as illustrated in FIG. 4, and the unit has a construction that the infrared cut filter 45, the condenser lens 46 and the light incident port 31 of the light guide 30 are arranged between the first focal point F1 and the second focal point F2.

As described above, as the spheroidal mirror making up the concave mirror 25A, that having the construction that the arrangement position of the light incident port 31 of the light guide 30 is located between the first focal point F1 and the second focal point F2 is used, whereby the projected light from the concave mirror 25A becomes light high in degree of parallelization, i.e., substantially parallel light. Therefore, the light applied to the infrared cut filter 45 becomes light high in degree of parallelization. In addition, the maximum incident angle of the projected light from the concave mirror 25A on the infrared cut filter 45 does not become large, or the degree becoming large is small even when the clearance between the light source 20 and the light guide 30 is made small for miniaturizing the light source unit 10. Accordingly, it is prevented that light large in incident angle is struck on the infrared cut filter 45.

In the spheroidal mirror making up the concave mirror 25A, the second focal point F2 is preferably located with a great space in the direction more separating from the first focal point F1 than the arrangement position of the light incident port 31 of the light guide 30.

The second focal point F2 is located with a great space in the direction more separating from the first focal point F1 than the arrangement position of the light incident port 31, whereby a clearance between the first focal point F1 and the second focal point F2 becomes great, and so the projected light from the concave mirror 25A becomes light higher in degree of parallelization, so that the light applied to the infrared cut filter 45 can be made light high in degree of parallelization.

The condenser lens 46 serves to condense transmitted light passed through the infrared cut filter 45 to cause the light to be struck on the light guide 30 and is provided farther onward in a traveling direction of the light in the optical path L1 than the infrared cut filter 45, i.e., at a position between the infrared cut filter 45 and the light incident port 31 of the light guide 30.

In this condenser lens 46, for achieving effective strike of the light on the light guide 30, the focal point F3 thereof is preferably located at a position more forward in the traveling direction of the light than the light incident port 31 of the light guide 30 and in a region contiguous to the light incident port 31.

When the spheroidal mirror is used as the concave mirror 25A, the focal point of the condenser lens 46 is preferably located between the arrangement position of the light incident port 31 of the light guide 30 and the second focal point F2 of the concave mirror 25A.

In the embodiment of this drawing, the focal point F3 of the condenser lens 46 is located on a straight line that links the first focal point F1 and the second focal point F2 of the concave mirror 25A and in a region in which the light guide 30 is surrounded by the light guide holding portion 13 between the light incident port 31 of the light guide 30 and the second focal point F2.

As the condenser lens 46, may be used a lens having a condensing function, specifically, for example, a convex lens.

Other constructions are the same as in the first embodiment.

In the light source unit 10 of such construction, the discharge lamp 21 making up the light source 20 is lit, whereby light emitted from the discharge lamp 21 is reflected on the concave mirror 25A, thereby being projected from the light projecting port, this projected light passes through the interior of the light shielding body 40 and is incident on the light guide 30 from the light incident port 31 through the infrared cut filter 45 and the condenser lens 46, and this light incident on the light guide 30 is guided by the light guide 30, thereby being emitted from the light outgoing port.

In the light source unit 10, the infrared cut filter 45 is provided in the light shielding body 40, so that infrared rays of the projected light from the concave lens 25A are reflected by the infrared cut filter 45 in the process that the projected light passes through the interior of the light shielding body 40, to inhibit the infrared rays from being struck on the liquid core fiber making up the light guide 30, thereby inhibiting the liquid core fiber from being heated by the infrared rays.

In the light source unit 10, as the infrared cut filter 45, is used a filter having an infrared reflecting layer formed of a multi-layer reflection film, and the infrared cut filter 45 of such construction is high in incident angle dependence of light transmission property (transmittance) from the viewpoint of the structure thereof, specifically, causes a wavelength shift that the spectral distribution of transmitted light of light struck at a large incident angle is shifted on a short wavelength side compared with the spectral distribution of transmitted light of light struck at a small incident angle. However, light high in degree of parallelization is projected from the concave mirror 25A, thereby preventing the light large in incident angle from being struck on the infrared cut filter 45, and the construction that the light high in degree of parallelization transmitted through the infrared cut filter 45 is condensed by the condenser lens 46, whereby the light can be struck on the light guide 30 as a high efficiency can inhibit the occurrence of such evils attributed to the use of the infrared cut filter equipped with the multi-layer reflection film as the following (1) and (2).

(1) The spectral distribution of transmitted light of light large in incident angle on the infrared cut filter is shifted on a short wavelength side compared with transmitted light small in incident angle, whereby the intensity of light on a long wavelength side in the light struck on the light guide becomes small, so that the light source unit cannot be applied to uses utilizing the light on the long wavelength side, or whereby the light struck on the light guide includes light on the short wavelength side of 300 nm or less, which may possibly adversely affect the component members of the liquid core fiber making up the light guide, so that the liquid core fiber is deteriorated or broken.

(2) When the projected light high in degree of parallelization is struck on the light guide as it is without being sufficiently condensed, the light emitted from the discharge lamp cannot be efficiently utilized, and the quantity of light struck on the light guide becomes small, so that sufficient illuminance is not achieved in the light emitted from the light guide.

As described above, according to the light source unit 10, the liquid core fiber making up the light guide 30 can be inhibited from being heated due to the incidence of the infrared rays, so that the light can be supplied by using the excellent optical properties that the liquid core fiber has without involving evils caused by heating the liquid core fiber, such as, for example, a phenomenon that the light from the light source 20 is not emitted from the light outgoing port of the light guide 30 during actuation, or a phenomenon that the light transmitting liquid 34 of the liquid core fiber making up the light guide 30 is deteriorated.

In the light guide unit 10, the spheroidal mirror is used as the concave mirror 25A, whereby there is no need to make the aperture 27 of the concave mirror 25A large for obtaining high light intensity in outgoing light from the light guide 30 because this spheroidal mirror can converge and project the light emitted from the discharge lamp 21 at a high efficiency without making the aperture 27 making up the light projecting port large, so that a high degree of freedom of design can be obtained to easily miniaturize the unit.

According to the light source unit 10 using the spheroidal mirror as the concave mirror 25A, as also apparent from Experimental Examples, which will be described subsequently, the light emitted from the discharge lamp 21 can be efficiently utilized, and high light intensity can be obtained in outgoing light from the light guide 30 though the unit is of a sufficiently miniaturized construction.

In the light source unit according to the second embodiment of the present invention, various changes or modifications may be added without being limited to the above-described embodiments.

For example, the spheroidal mirror is preferably used as the concave mirror in the light source unit because the degree of freedom of design is high, and the light source unit can be easily miniaturized. However, a paraboloidal mirror may also be used.

In addition, when the spheroidal mirror is used as the concave mirror in the light source unit, a lens whose focal point is located between the arrangement position of the light incident port of the light guide and the second focal point of the spheroidal mirror is preferably used as the condenser lens because the light can be efficiently struck on the light guide. However, it is only necessary that the focal point is located with a space in a direction more separating from the first focal point of the spheroidal mirror than the arrangement position of the light incident port of the light guide, and so a lens whose focal point is located with a space in a direction more separating from the first focal point of the spheroidal mirror than the second focal point of the spheroidal mirror may also be used.

Experimental Examples that were conducted for confirming actions and effects in the second embodiment of the present invention will hereinafter be described.

Experimental Example 3

An light source unit (hereinafter also referred to as "light source unit (3)") was fabricated according to FIG. 4, and a light source unit (hereinafter also referred to as "comparative light source unit (3)") having the same construction as in the light source unit (3) except that no condenser lens was provided was fabricated.

As a light source making up the light source unit (3) and comparative light source unit (3) fabricated, was used the following. An extra-high pressure mercury lamp whose rated power consumption is 130 W was used as a discharge lamp, a spheroidal mirror which reflects and converges light within a wavelength range up to 800 nm, the clearance between the second focal point and the light projecting port of which is 100 mm, was used as a concave mirror, and these were arranged in such a manner that the first focal point of the concave mirror (spheroidal mirror) is located at the position of a luminescent spot of the discharge lamp (extra-high pressure mercury lamp).

In the light source unit (3) and comparative light source unit (3), a liquid core fiber manufactured by LUMATEC CO was used as a light guide, a filter that has an infrared reflecting layer formed of a multi-layer reflection film composed of titanium oxide ($TiO_2$) and silica ($SiO_2$) and transmits light having a wavelength of 360 to 700 nm and reflects light (light having a wavelength of 750 to 1,150 nm) on a longer wavelength side than the above range was used as an infrared cut filter, and a plano-convex lens having a focal distance of 30 mm was used as a condenser lens in the light source unit (3).

In the light source unit (3) and comparative light source unit (3), a clearance between the light source and the light guide them, i.e., a clearance between the light projecting port in the light source and the ling incident port in the light guide is 97 mm, and a maximum incident angle of projected light from the concave mirror on the infrared cut filter is 13.5°. The second focal point of the concave mirror (spheroidal mirror) is located with a space in a direction more separating from the first focal point than the arrangement position of the light incident port of the light guide. The focal point of the condenser mirror is located behind the light incident port of the light guide in the traveling direction of the projected light from the concave mirror (spheroidal mirror), and a clearance between the light incident port and the focal point of the condenser lens is 18.1 mm.

With respect to the light source unit (3) and comparative light source unit (3), the quantity of light struck on the light incident port of the light guide was measured. As a result, the quantity of the light in the light source unit (3) was larger than the comparative light source unit (3). Specifically, the quantity of the light struck on the light incident port in the light source unit (3) was 1.8 in terms of a relative value that the reference value of the quantity of the light struck on the light incident port in the comparative light source unit (3) was regarded as 1.0.

From the result of Experimental Example 3, it was confirmed that even when the concave mirror projects light high in degree of parallelization, the light high in degree of parallelization is condensed by the condenser mirror, whereby the light can be struck on the light guide in a high light quantity.

Experimental Example 4

In a construction that a paraboloidal mirror was used in place of the spheroidal mirror in the light source unit (3) fabricated in Experimental Example 3, and the paraboloidal mirror was arranged in such a manner that the focal point thereof is located at the position of a luminescent spot of the discharge lamp, the diameter of an aperture making up a light projecting port in the paraboloidal mirror was adjusted, thereby fabricating a light source unit (hereinafter also referred to as "light source unit (4)") by which the quantity of light struck on the light incident port of the light guide became equal to that of the light source unit (3).

With respect to the light source unit (4) fabricated, the diameter of the aperture of the paraboloidal mirror was confirmed. As a result, the diameter was large compared with the diameter of the aperture of the spheroidal mirror making up the light source unit (3). Specifically, the diameter of the aperture of the concave mirror (paraboloidal mirror) of the light source unit (4) was 1.30 in terms of a relative value that the reference value of the diameter of the aperture of the spheroidal mirror of the light source unit (3) was regarded as 1.0.

From the result of Experimental Example 4, it was confirmed that the spheroidal mirror was used as the concave mirror, whereby the projected light from the discharge lamp can be converged and projected at a high efficiency without making the aperture making up the light projecting port large compared with the case where the paraboloidal mirror was used as the concave mirror, and so a high degree of freedom of design can be obtained to easily miniaturize the unit.

| REFERENCE SIGNS LIST | |
|---|---|
| 10 | Light source unit |
| 11 | Casing |
| 11A | Top portion |
| 11B | Bottom portion |
| 11C, 11D, 11E, 11F | Side wall portions |
| 12 | Lamp holding portion |
| 13 | Light guide holding portion |
| 14A | Cooling air inlet |

-continued

| REFERENCE SIGNS LIST | |
|---|---|
| 14B | Cooling air outlet |
| 17 | Light quantity adjusting member |
| 17A | Light shielding plate |
| 17B | Light passage aperture |
| 19 | Cooling fan |
| 20 | Light source |
| 21 | Discharge lamp |
| 22 | Light emitting tube |
| 22A | Light emitting portion |
| 22B | Sealing portion |
| 23 | Electrode |
| 25 | Converging mirror |
| 25A | Concave mirror |
| 26 | Converging portion |
| 27 | Aperture |
| 30 | Light guide |
| 31 | Light incident port |
| 33 | Cladding |
| 34 | Light transmitting liquid |
| 36 | Rod |
| 38 | Flexible metal sheath |
| 39A | Metal ferrule |
| 39B | Gasket |
| 40 | Light shielding body |
| 41A, 41B | Openings |
| 45 | Infrared cut filter |
| 46 | Condenser lens |
| 48 | Support for light shielding body |
| 52 | Light guide |
| 53 | Light incident port |

The invention claimed is:

1. A light source unit comprising:
a light source having a discharge lamp and a converging mirror converging light from the discharge lamp;
a light guide on which the light from the light source is incident; and
a casing which is made of a metal and which holds the light source and the light guide,
wherein:
the light guide comprises a liquid core fiber with a light transmitting liquid filled into a cladding,
the light source and the light guide are held by a light source holding portion and a light guide holding portion, respectively, in the casing,
the casing is equipped with a cylindrical light shielding body which is supported by a support for the light shielding body which is fixed to the casing, and the light shielding body surrounds an optical path extending from the light source to the light guide in an interior of the casing,
an infrared cut filter is provided in the light shielding body so as to be located on the optical path from the light source to the light guide,
the light shielding body forms a stray light preventing member which prevents stray light generated in the interior of the casing from going out of the casing,
a light quantity adjusting member is provided at a position between an opening of the light shielding body on a light guide side and a light incident port of the light guide, and
a heat insulating material portion formed of a heat insulating material is interposed between the light shielding body and the light guide holding portion, so that the light shielding body and the light guide holding portion are thermally insulated from each other.

2. The light source unit according to claim 1, wherein the support is formed of the heat insulating material, and the support forms the heat insulating material portion.

3. The light source unit according to claim 1, wherein the heat insulating material has a heat conductivity of 3 [W·m−1·K−1] or less.

4. The light source unit according to claim 1, wherein a cooling air inlet and a cooling air outlet are provided in the casing to cool the light shielding body by cooling air from a cooling fan.

5. The light source unit according to claim 2, wherein a cooling air inlet and a cooling air outlet are provided in the casing to cool the light shielding body by cooling air from a cooling fan.

6. The light source unit according to claim 3, wherein a cooling air inlet and a cooling air outlet are provided in the casing to cool the light shielding body by cooling air from a cooling fan.

* * * * *